| United States Patent [19] | [11] 3,974,103 |
| --- | --- |
| Kaiser | [45] Aug. 10, 1976 |

[54] CATALYST FOR ISOMERIZATION OF ALPHA-PINENE TO BETA-PINENE

[75] Inventor: Gregory L. Kaiser, West Jacksonville, Fla.

[73] Assignee: SCM Corporation, New York, N.Y.

[22] Filed: May 12, 1975

[21] Appl. No.: 576,718

[52] U.S. Cl. .................. 252/466 J; 252/466 PT; 260/675.5
[51] Int. Cl.$^2$ ................. B01J 21/04; B01J 23/58; B01J 23/78
[58] Field of Search ............... 252/466 PT, 466 J; 260/675.5

[56] References Cited
UNITED STATES PATENTS

| 3,150,206 | 9/1964 | Miller et al. ............ 252/466 J |
| 3,278,623 | 10/1966 | Derfer ..................... 260/675.5 |
| 3,679,746 | 7/1972 | Brake ..................... 252/466 PT |

FOREIGN PATENTS OR APPLICATIONS

| 814,003 | 5/1959 | United Kingdom ........... 252/466 PT |

*Primary Examiner*—W. J. Shine
*Attorney, Agent, or Firm*—Jerry K. Mueller, Jr.

[57] ABSTRACT

The acidic functionality displayed by an alumina-supported catalyst is neutralized in a neutralization treatment with an alkali metal or alkaline earth metal salt or hydroxide. The neutralized alumina-supported catalyst is especially useful in the catalyzed isomerization of alpha-pinene to beta-pinene.

12 Claims, No Drawings

CATALYST FOR ISOMERIZATION OF ALPHA-PINENE TO BETA-PINENE

This invention relates to an alumina supported Group VIII catalyst for the catalyzed isomerization of alpha-pinene to beta-pinene and more particularly to neutralizing the acidic functionality of such alumina-supported Group VIII catalyst to increase the selectively for beta-pinene formation.

BACKGROUND OF THE INVENTION

The catalyzed isomerization of alpha-pinene to beta-pinene to which this invention is directed is disclosed in U.S. Pat. No. 3,278,623, the disclosure of which is expressly incorporated herein by reference. The isomerization is carried out in the presence of a transitory hydrogen acceptor catalyst using hydrogen gas as a co-catalyst. A preferred such hydrogen acceptor catalyst is a Group VIII metal on an alumina support. Such isomerization process is acutely acid sensitive as acidic conditions in the process can deactivate the otherwise active Group VIII catalyst and will cause formation of undesirable by-products (such as camphene, cymene, and limonene). Formation of such by-products (hereinafter referred to as acidic or acid by-products) during the alpha-pinene isomerization process decreases the selectivity of the alumina-supported Group VIII catalyst for beta-pinene formation.

Commercially prepared alumina-supported Group VIII catalysts can have residual anions thereon, which anions can form acid in the presence of hydrogen. Such commercial preparation generally comprises treating alumina with an aqueous salt solution of the Group VIII catalyst followed by drying and a subsequent reduction in a basic hydrazine solution or in flowing hydrogen gas. Residual anions remain on the alumina supported Group VIII catalyst even after the reduction step. These residual anions can form acid when contacted with the co-catalyst hydrogen gas during the isomerization process which can cause the aforementioned by-product formation.

The Group VIII catalyst salts can include the salts of chlorine, bromine iodine, fluorine, nitrate, sulfate and the like. The chloride salts of the Group VIII catalyst are commonly used in such commercial preparations and this invention will be described with reference to chloride salt preparation of the alumina-supported Group VIII catalyst.

Most of the various forms of alumina readily hydrate to form acid sites (hydroxyl groups) thereon which hydroxyl groups can serve as a source of protons, the alumina displaying acidic functionalities thereby. The residual chloride ions further can exchange with such hydroxyl groups which exchange intensifies the electronegativity of the acid sites. Heretofore, it has been proposed to neutralize these acid sites of an alumina catalyst (as distinguished from an alumina-supported catalyst) by treating the alumina with amines. Herman Pines and C. N. Pillai in "Alumina: Catalyst and Support X. Modification of Alumina by Bases. Mechanism of Dehydration of Menthol and Neomenthol," Journal American Chemical Society, Volume 83, pp. 3070–3274 (1961) describe treating an alumina catalyst with amines such as ammonia, trimethylamine, and pyridine in order to neutralize the acid sites on such alumina catalysts. However, when the alumina serves as a support for a catalyst, such as elemental palladium, amines deactivate the palladium catalyst for the alpha-pinene isomerization process.

For purposes of this application, selectivity is measured as a function of the acid by-products formed during the isomerization process. By suppressing such acid by-products, selectivity of the supported catalyst is increased. Selectivity is calculated as follows:

$$\text{Selectivity} = \frac{\%\ \text{beta-pinene yield}}{\%\ \text{alpha-pinene totally converted}} \times 100\%$$

wherein % alpha-pinene totally converted includes beta-pinene and acid by-products. It is readily apparent that as the percent of acidic by-products is decreased, the selectivity approaches 100%.

Acid by-products in addition cause difficulty in effecting a clean separation of the beta-pinene from unconverted alpha-pinene and also decrease the amount of alpha-pinene available for recycle as well as contaminate such alpha-pinene recycle.

DESCRIPTION OF THE INVENTION

The present invention resides in the discovery that the foregoing disadvantages of acid functionality displayed by the alumina-supported Group VIII catalyst due generally to residual anions on the alumina-supported Group VIII catalyst, capable of forming acid in the presence of molecular hydrogen, and acid sites on the alumina support of an alumina-supported Group VIII catalyst can be overcome by subjecting the alumina-supported catalyst to a neutralization treatment as disclosed herein.

Also disclosed herein is an improved alumina-supported Group VIII catalyst which displays substantially no acidic functionality, even in the presence of hydrogen, such supported catalyst being especially useful in the catalyzed isomerization of alpha-pinene to beta-pinene where neutral to basic conditions must be maintained in order to suppress acid by-product formation during such isomerization.

The alumina-supported Group VIII catalyst is treated with at least about 0.002 weight parts per weight part of alumina of an alkali metal or alkaline earth metal neutralizing agent provided from an alkali metal or alkaline earth metal salt or hydroxide (neutralizing agent salt or hydroxide) inert to the catalyst. For purposes of this application "alkali metal" means sodium, lithium, potassium, rubidium, and cesium; and "alkaline earth metal" means calcium, strontium, barium, and magnesium.

Treatment with about 0.002 weight parts of the neutralizing agent generally is sufficient to affect a significant neutralization of the acid functionality displayed by the supported catalyst and concomitant suppression of most of the acid by-product formation during the alpha-pinene isomerization process. Treatment with about 0.015 weight parts of neutralizing agent per weight part of alumina substantially neutralizes the acid functionality displayed by the supported catalyst and above about 0.015 weight parts waste of the neutralizing agent can occur, though activity and selectivity of the supported catalyst normally will not be adversely effected by such treatment levels above 0.015 weight parts.

The alkali metal or alkaline earth metal salt or hydroxide is preferably dispersed in a solvent for treating the supported catalyst. Water is a preferred solvent and, thus, some water solubility of the neutralizing agent is desirable. If the particular neutralizing agent is only slightly soluble in water, successive treatments of the alumina-supported catalyst may be necessary to effectively substantially neutralize the alumina-supported catalyst's acid functionality. Such successive treatments are not injurious to the catalyst supported on the alumina, and in some instances it is desirable to so successively treat the catalyst in order to attain complete neutralization. The amount of water should be sufficient to satisfy the pore volume of the alumina.

Preferable suitable neutralizing agents include, for example, alkali metal or alkaline earth metal carbonates, bicarbonates, hydroxides, nitrates, nitrites, acetates, formates, and oxylates and the like.

The treated supported catalyst then is heated at a temperature of less than about the minimum sintering temperature of the catalyst. For purposes of this application, the minimum sintering temperature is the temperature above which the crystalline size of the catalyst will be altered and such catalyst rendered unsuitable for use in the isomerization of alpha-pinene.

The anions of the salts (neutralizing agent salt anions) can combine with cocatalyst hydrogen during the alpha-pinene isomerization process to form their corresponding acid, which acid is deleterious to the isomerization process. The anions of the hydroxides (hydroxyl groups of neutralizing agents) can combine with the hydrogen to form water. The presence of water during the isomerization is best avoided in order to aid in separation of the products formed during the isomerization.

To rid the supported catalyst of these anions, the heating of the treated supported catalyst is done in the presence of hydrogen, as such anions form compounds with the hydrogen which are readily fugitive or decomposable at elevated temperatures. The temperature of heating, therefore, should be sufficient to volatilize or decompose the compound formed by the anion of the salt or hydroxide with hydrogen, and a temperature of less than about 180°C generally will be sufficient.

The hydrogen can come from the hydroxyl group on the alumina support (acid site) or can come from hydrogen gas contacting the treated supported catalyst during the heating step.

Preferably, the treated supported catalyst is heated in the presence of hydrogen gas in order to insure that substantially all of the anions are combined with hydrogen to form the corresponding compound which can be evaporated under such heating.

In a specific example, treatment with sodium carbonate causes formation of carbonic acid, which readily decomposes to carbon dioxide and water under moderate heating of about 100°C. Applicant theorizes that when other neutralizing agents, such as sodium acetate, are employed in the treatment, that a corresponding anion, such as an acetate anion, is formed. Heating the treated alumina-supported catalyst at about 120°C and 1 atmosphere total pressure then causes the corresponding acid, such as acetic acid, to be formed and such acid readily evaporates to yield a neutralized alumina-supported catalyst free of such anion.

While applicant does not intend to be bound by the following, it appears that the alkali metal or alkaline earth metal forms a corresponding chloride salt when the supported catalyst is treated with the alkali metal or alkaline earth metal salt or hydroxide. Such alkali metal or alkaline earth metal chloride salts need not be removed from the supported catalyst prior to the isomerization process as such salts are not chemically deleterious to the isomerization process.

Applicant further believes that during the neutralization treatment the alkali metal or alkaline earth metal reacts with the hydroxyl sites on the alumina to form a corresponding oxide of the alkali metal or alkaline earth metal and the disassociated hydrogen from the hydroxyl group combines with the anion of the salt or hydroxide to form the corresponding acid or water which is volatile or decomposable under conditions of heating. At least a portion of the acid sites, then, are neutralized by the treatment.

A theory explaining the formation of atomic hydrogen on alumina has been proposed by Kenneth M. Sancher in "Hydrogen Migration of Alumina/Palladium Catalysts for Benzene Hydrogenation," Journal of Catalysis, Vol. 20, pages 106–109 (1971), the same being incorporated herein by reference. Such proposal is that hydrogen atoms can come from chemisorbed hydrogen on the catalyst, which hydrogen migrates to the alumina support. Applicant theorizes that such migrated hydrogen combines with the hydroxyl group to form an acid site (Broensted acid site) on the alumina support.

The preferred catalysts suitable for the alpha-pinene isomerization process supported on an alumina support, are those elemental metals disclosed in U.S. Pat. No. 3,278,623, which are the Group VIII metals having an atomic number between 28 and 78, inclusive, (nickel, ruthenium, rhodium, palladium, osmium, irridium and platinum). The preferred catalyst is elemental palladium and in this application the catalyst will be described with reference to palladium, although it will be apparent to those skilled in the art that other catalysts may be employed.

Alumina appears in various crystalline structures, such as alpha-alumina, theta-alumina, delta-alumina, gamma-alumina, etc., as more fully described in Kirk-Othmer, Encyclopedia of Chemical Technology, Vol. 2, second Edition, the same being incorporated herein by reference. The particular crystalline structure of the alumina for the alpha-pinene isomerization process is not critical. Various combinations of the different crystalline forms of the alumina also are beneficial as will become apparent from the examples of this application.

The preferred aluminas are gamma-alumina and alpha-alumina, the former when used for the catalyst support providing the highest conversion to beta-pinene compared to other forms of alumina. Alpha-alumina on the other hand is the most effective form of alumina in suppressing formation of acid by-products. Thus, the greatest selectivity for beta-pinene formation is obtained by using alpha-alumina as the support for the catalyst as will be seen from the examples of this application. Alpha-alumina is chemically the most stable form of alumina and is resistant to forming hydroxyl acid sites thereon.

The isomerization reaction then is carried out in a suitable vessel having means for supporting the catalyst, by passing a stream of alpha-pinene in vapor or liquid form over the neutralized alumina-supported catalyst. A preferred carrier for the alpha-pinene stream is helium, with which is mixed about 2.0–8.0% hydrogen, as a co-catalyst, based on the moles of alpha-pinene being subjected to isomerization. Details of the catalyzed isomerization of alpha-pinene can be as practiced in U.S. Pat. No. 3,278,623.

The initial alpha-pinene supply may contain contaminants, such as sulphur, which poisons the catalyst during isomerization. Thus, it may be desirable to remove such contaminates in the alpha-pinene supply by pretreating such supply in accordance with the teachings of U.S. Pat. Nos. 3,325,553; 3,360,581; and 3,420,910, the same being incorporated herein by reference.

The following examples show in detail how the invention has been practiced, but should not be construed as limiting. In this specification, all parts are parts by weight, all percentages are weight percentages, and all temperatures are in degrees centigrade unless otherwise expressly indicated.

EXAMPLES

In all examples of this application alpha-pinene was isomerized to beta-pinene according to the teachings of U.S. Pat. No. 3,278,623 under the following conditions.

| | |
|---|---|
| Reactor: | ⅜" I.D. by 5" pyrex tube with medium glass frit to support the catalyst |
| Catalyst: | 2.0 grams of 1% Pd by weight of the alumina on various aluminas. |
| Co-Catalyst: | Hydrogen gas, %H$_2$ expressed as molar ratio of H$_2$/alpha-pinene, varied between 0 and 7.5% |
| Reaction Temperature: | 150°C. |
| Alpha-pinene Supply: | gas, admitted to reactor at 2.8–3.0 Torr (mmHg) effectively sulfur-free supply |
| Carrier: | helium gas |
| Contact time over Catalyst: | 0.38 seconds |
| Selectivity for beta-pinene: | $\frac{\% \text{ beta-pinene formed}}{\% \text{ alpha-pinene totally converted}} \times 100\%$ |

The supported catalysts employed in the following examples had been prepared by contacting the various aluminas with an aqueous palladium chloride solution followed by drying and reduction. A representative reaction procedure for preparing an alpha-alumina supported palladium catalyst (1% palladium by weight of the alumina) is as follows:

1. 1.67 gms. of palladium chloride is dissolved in 35 gms. of water;
2. the aqueous PdCl$_2$ solution is added to 100 gms. of alpha-alumina (⅛ inch tablets);
3. the PdCl$_2$-treated alumina is dried over a steam bath to remove substantially all of the water;
4. 0.15 gms. of hydrazine (N$_2$H$_4$) is added to a 0.5 N aqueous sodium hydroxide solution (35 gms. of caustic);
5. the hydrazine solution is added to the alumina with PdCl$_2$ disposed thereon and gently agitated at room temperature for 30 minutes; and
6. the hydrazine solution is drained off the supported catalyst and the supported catalyst is washed with water and dried to remove substantially all of the moisture therefrom.

EXAMPLE 1

As a control, alpha-pinene was isomerized to beta-pinene over 1% palladium catalyst disposed on various crystalline alumina supports, which alumina supported palladium catalyst was not neutralized according to the precepts herein. The supported catalysts were heated in a stream of helium plus alpha-pinene and 0.1% hydrogen (based on the moles of pinene) to reaction temperature. The various crystalline aluminas were gamma-alumina (⅛ inch tablets), 65% alpha + 35% theta alumina (3 mm spheres), and alpha-alumina (⅛ inch tablets). Table 1 gives the results obtained in terms of moles of hydrogen consumed, grams of products obtained, and selectivity.

TABLE 1

| Alumina Support | %H$_2$ | beta-pinene | Pinanes | Camphene | Limonene+Others | | Select. |
|---|---|---|---|---|---|---|---|
| gamma-alumina | 0.9 | 4.5 | 0.2 | 0.6 | 0.5 | 1.2 | 64.2 |
| (65% alpha + 35% theta)-alumina | 1.9 | 2.8 | 0.05 | 0.4 | 0.4 | — | 77.4 |
| alpha-alumina | 1.9 | 2.3 | — | 0.3 | — | — | 90.0 |

EXAMPLE 2

Various alumina supports like those of Example 1 having 1% palladium supported thereon were treated with an aqueous solution of sodium carbonate in order to suppress the acid functionality of the alumina. Sufficient sodium carbonate was used in order to supply 0.002 grams of sodium per gram of alumina support after evaporation of the water. Sufficient distilled water was used to satisfy the pore volume of each different alumina. The sodium carbonate treated supported catalyst was dried in an oven at 100°–150° for 1 hour. The reaction conditions were as above detailed. Table II gives the results obtained.

TABLE II

| Alumina Support | %H$_2$ | beta-pinene | Pinanes | Camphene | Limonene Cymene | Others | Selec. |
|---|---|---|---|---|---|---|---|
| gamma-alumina (65% alpha + 35% | 1.4 | 3.1 | 0.08 | 0.10 | 0.04 | — | 93.0 |

TABLE II-continued

| Alumina Support | %H₂ | beta-pinene | Pinanes | Camphene | Limonene Cymene | Others | Selec. |
|---|---|---|---|---|---|---|---|
| theta-alumina | 3.7 | 2.84 | 0.04 | 0.40 | — | — | 86.6 |
| alpha-alumina | 3.7 | 2.75 | 0.01 | — | — | — | 99.6 |

Comparison of the results of Tables I and II shows that at least about a 10% increase in beta-pinene selectivity is obtained by the sodium carbonate treatment of the alumina supported catalyst. It should be noted that camphene cannot be entirely eliminated even using an unsupported palladium catalyst and, thus, is not solely a product of the alumina's acidity.

The average crystalline sizes of the palladium used in Examples 1 and 2 on the alumina supports varied for the different supports. In order to substantially equalize the amount of co-catalyst hydrogen available for the palladium of various crystalline sizes, different hydrogen concentrations (% $H_2$) were used, as can be seen in Tables 1 and 2. The selectivity comparisons are not functions of the varying amounts of hydrogen used, but are products substantially solely due to the palladium catalyst and affect of the neutralization treatments thereof.

EXAMPLE 3

To determine the effect of successive sodium carbonate treatments on the selectivity and activity of the alumina supported palladium catalyst, a sample of the alpha-alumina supported palladium catalyst was incrementally treated with successive treatments of sodium carbonate at the rate of 0.002 grams of sodium based on the weight of alumina support after evaporation of water. Such treatment and drying of the supported catalyst was carried out in the same manner employed in Example 2. Table III gives the results obtained:

TABLE III

| Grams of Sodium per gram of alumina | %H | beta-pinene | Pinanes | Camphene | Limonene+ Cymene | Other | Selec. |
|---|---|---|---|---|---|---|---|
| 0 | 3.7 | 2.5 | 0.04 | 1.60 | 1.64 | 0.03 | 42.8 |
| .002 | 3.7 | 2.6 | — | 0.29 | 0.02 | — | 89.3 |
| .004 | 3.7 | 2.6 | 0.03 | 0.29 | — | 0.03 | 87.8 |
| .006 | 3.7 | 2.5 | 0.09 | 0.04 | — | 0.07 | 92.5 |

The above results show that successive sodium carbonate treatments serve to reduce the acid by-products formed while the amount of beta-pinene formed and beta-pinene selectivity remains relatively constant.

EXAMPLE 4

A 1% palladium catalyst supported on alpha-alumina was treated with 0.005 grams of sodium acetate per gram of alpha-alumina. The sodium acetate was in aqueous solution. The treated supported catalyst was heated at 185°C. for 3 hours in the presence of flowing hydrogen gas (1 atmosphere total pressure).

A substantially identical 1% palladium catalyst supported on alpha-alumina was used as a control except that it had not been subjected to a neutralization treatment. The results obtained by employing the above catalysts in the alpha-pinene isomerization process are given in Table IV.

TABLE IV

| | %H₂ | beta-pinene | Pinanes | Camphene | Selectivity |
|---|---|---|---|---|---|
| Control Catalyst | 6.2 | 3.84 | 0.17 | 0.11 | 91.2 |
| Sodium Acetate Neutralized Catalyst | 4.5 | 3.80 | 0.15 | — | 96.2 |

The above tabled results show that the selectivity of the supported catalyst is increased by the sodium acetate neutralization treatment by suppressing some acid by-product formation.

I claim:

1. A process for neutralizing the acidic functionality displayed by an alumina-supported Group VIII catalyst, wherein said Group VIII catalyst is disposed on said alumina support by contacting said alumina support with a Group VIII salt solution followed by drying and reduction, said reduced alumina-supported catalyst having residual anions remaining thereon, said Group VIII catalyst being an elemental Group VIII metal having an atomic number between 28 and 78, inclusive, and said anions forming acid when contacted by hydrogen, which comprises:
   a. treating said alumina supported catalyst with at least about 0.002 weight parts per weight part of said alumina support of an alkali metal or alkaline earth metal provided from a salt or hydroxide of an alkali metal or alkaline earth metal inert to said catalyst; said treatment resulting in the formation of a salt of an alkali metal or alkaline earth metal with said residual anions; and
   b. heating said treated alumina supported catalyst in the presence of hydrogen at a temperature less than about the minimum sintering temperature of said catalyst, the temperature of said heating being sufficient to volatilize or decompose the compound formed by the anion of said salt or hydroxide and said hydrogen.

2. The process of claim 1 wherein said elemental Group VIII metal is selected from the group consisting of palladium, platinum, nickel, ruthenium, and rhodium.

3. The process of claim 2 wherein said elemental Group VIII metal is palladium and said minimum sintering temperature is about 400°C.

4. The process of claim 3 wherein said alumina is alpha-alumina.

5. The process of claim 1 wherein said alkali metal or alkaline earth metal salt or hydroxide is in solution form.

6. The process of claim 1 wherein said alumina support has acid sites and at least a portion of said acid sites are neutralized by said treatment.

7. An alumina-supported Group VIII catalyst wherein said Group VIII catalyst is disposed on said alumina support by contacting said alumina support with a Group VIII salt solution followed by drying and reduction, said reduced alumina-supported Group VIII catalyst having residual anions remaining thereon, said Group VIII catalyst being an elemental Group VIII metal having an atomic number between 28 and 78, inclusive, the improvement wherein said alumina-supported catalyst is neutralized following said reduction by treatment with at least about 0.002 weight parts per weight part of said alumina support of an alkali metal or alkaline earth metal provided from a salt or hydroxide of an alkali metal or alkaline earth metal, said treatment resulting in the formation of a salt of an alkali metal or alkaline earth metal with said residual anions, followed by heating in the presence of hydrogen at a temperature less than about the minimum sintering temperature of said Group VIII catalyst, but at a temperature sufficient to volatilize or decompose the compound formed by the anion of said salt or hydroxide with said hydrogen.

8. The alumina supported Group VIII catalyst of claim 7 wherein said elemental Group VIII metal is selected from the group consisting of palladium, platinum, nickel, ruthenium, and rhodium 9. The alumina supported Group VIII catalyst of claim 8 wherein said elemental Group VIII metal is palladium.

10. The alumina-supported Group VIII catalyst of claim 7 wherein said alumina support has acid sites thereon and at least a portion of said acid sites are neutralized by said treatment.

11. The alumina supported Group VIII catalyst of claim 10 wherein said elemental Group VIII catalyst is selected from the group consisting of palladium, platinum, nickel, ruthenium, and rhodium.

12. The alumina supported Group VIII catalyst of claim 11 wherein said elemental Group VIII metal is palladium.

* * * * *